United States Patent
Evans et al.

(10) Patent No.: US 8,293,939 B2
(45) Date of Patent: Oct. 23, 2012

(54) METHODS FOR REMOVING VICINAL DIOLS FROM LACTIC ACID FERMENTATION BROTH

(75) Inventors: Chana W. Evans, Saginaw, MI (US); Ralph B. Fogg, Midland, MI (US); James H. Hand, Midland, MI (US); Anthony Revis, Freeland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/255,421

(22) PCT Filed: Feb. 24, 2010

(86) PCT No.: PCT/US2010/025212
§ 371 (c)(1),
(2), (4) Date: Sep. 8, 2011

(87) PCT Pub. No.: WO2010/104677
PCT Pub. Date: Sep. 16, 2010

(65) Prior Publication Data
US 2012/0029231 A1 Feb. 2, 2012

Related U.S. Application Data

(60) Provisional application No. 61/158,479, filed on Mar. 9, 2009.

(51) Int. Cl.
*C07C 51/42* (2006.01)
*C07C 51/47* (2006.01)

(52) U.S. Cl. ...................................................... 562/580

(58) Field of Classification Search .................. None
See application file for complete search history.

(56) References Cited

U.S. PATENT DOCUMENTS

| | | | |
|---|---|---|---|
| 5,426,219 A | 6/1995 | Lehnhardt | 562/580 |
| 5,643,602 A | 7/1997 | Ulmius | 424/462 |
| 5,922,449 A | 7/1999 | Revis | 428/306.6 |
| 7,125,488 B2 | 10/2006 | Li | 210/198.2 |
| 2005/0233031 A1 | 10/2005 | Hughes | 425/52 |
| 2006/0204576 A1 | 9/2006 | Petereit et al. | 424/472 |
| 2007/0172913 A1 | 7/2007 | Hughes et al. | 435/41 |

FOREIGN PATENT DOCUMENTS

| | | |
|---|---|---|
| CN | 101274876 | 10/2008 |
| EP | 0135728 | 4/1985 |
| EP | 2017347 | 1/2009 |
| JP | 51-012990 | 1/1976 |
| JP | 58-056690 | 4/1983 |
| WO | WO 96/41021 | 12/1996 |
| WO | WO 00/17378 | 3/2000 |

OTHER PUBLICATIONS

Machine translation of CN 101274876 published in 2008.*
Bai et al. "Determination of Lactic Acid in Fermentation Broth of Rhizopus Oryzae by Reversed-Phase High Performance Liquid Chromatorgraphy (RP-HPLC)." Chinese Journal of Chromatography. vol. 18, No. 6, Nov. 2000 (1 page).
Duke et al. "High Selectivity Microporous Silica Membranes for Lactic Acid Fermentation." A1ChE Spring National Meeting, Conference Proceedings, Orland, FL, Apr. 23-27, 2006, American Institute of Chemical Engineers (6 pages).
Guenzel et al. "Adsorption von Diolen aus Fermentationsmedien an hydrophobe Zeolithe." Chemie Ingenieur Technik. vol. 62, No. 1, Sep. 1, 1990 (pp. 748-750).
Huang et al. "Method for Adsorptive Separating 2, 3-butanediol from Fermentation Liquor by Using Hydrophobic Zeolite." Database WPI Week 200907 [retrieved on Aug. 30, 2010]. Retrieved from: Thomson Scientific, London, GB; Accession No. 2009-B11836 (XP002590108) (2 pages).
Li et al. "Optimization of L(+)-Lactic Acid Fermentation without Neurtralisation of Rhizopus Oryzae Mutant RK02 by Low-Energy Ion Implantation." Plasma Science and Technology. vol. 10, No. 2, Apr. 2008 (5 pages).
International Search Report, mailed Sep. 3, 2010, issued in corresponding International Patent Application No. PCT/US2010/025212 (7 pages).
Written Opinion, mailed Sep. 3, 2010, issued in corresponding International Patent Application No. PCT/US2010/025212 (6 pages).

* cited by examiner

*Primary Examiner* — Yevegeny Valenrod
(74) *Attorney, Agent, or Firm* — Nixon Peabody LLP

(57) ABSTRACT

Embodiments of a method for removing vicinal diols from a lactic acid fermentation broth comprise the steps of contacting the lactic acid fermentation broth with functionalized silica comprising at least one hydrophobic ligand to facilitate binding of the vicinal diols to the hydrophobic ligand, and separating the contacted lactic acid fermentation broth from the functionalized silica to remove the vicinal diols.

18 Claims, No Drawings

METHODS FOR REMOVING VICINAL DIOLS FROM LACTIC ACID FERMENTATION BROTH

CROSS REFERENCE TO RELATED APPLICATIONS

This application is a U.S. national stage of International Application No. PCT/US2010/025212, filed Feb. 24, 2010, which claims priority to U.S. Provisional Application No. 61/158,479 filed on Mar. 9, 2009, which is incorporated herein in its entirety.

Embodiments of the present invention are generally directed to methods of removing 2,3-butanediol from a lactic acid fermentation broth, and are specifically directed to removing 2,3-butanediol from a lactic acid fermentation broth via the binding of vicinal diols, such as 2,3-butanediol, to a functionalized silica comprising a hydrophobic ligand.

Manufacture of lactic acid, a precursor to the biodegradable polymer polylactic acid (PLA), is typically done by fermentation of glucose and other sugars using various strains of bacteria, for example, lactobacillus bacteria. However, during the fermentation process, the bacteria becomes inhibited by the lactic acid product so that the reaction slows and eventually stops. To overcome this obstacle, a base may be added continuously to produce a salt of lactic acid. The salt does not inhibit the bacteria, but the product must be converted back to lactic acid or a cyclic lactate for polymerization.

After fermentation, the output of the fermentor may include the lactate salt product, cells, cellular debris, by-products, unreacted sugars, and fermentation media. The lactic acid salt can be converted to the free acid form by adding a strong acid, and then be extracted from the fermentation media using an amine solution. Cells and solid debris can be removed in a filtration step, usually using a filter aid; however, the removal of small by-product contaminants such as other organic acids and organic diols from the lactic acid remains challenging. These contaminants may interfere with the subsequent polymerization process, and must be removed from the lactic acid feed stream. Accordingly, improved systems and methods for removing contaminants (e.g., organic diols such as 2,3-butanediol) from a lactic acid fermentation broth are desirable.

Embodiments of the present invention are generally directed to the removal of or reduction in the amount of vicinal diols including 2,3 diols, specifically 2,3-butanediol, in a lactic acid fermentation broth through the use of filter media comprising functionalized silica, specifically, silane functionalized silica comprising a C4-C18 hydrophobic ligand. As defined herein, a vicinal diol is any diol in which the two hydroxyl functional groups are attached to adjacent carbon atoms.

According to one embodiment, a method of removing 2,3-butanediol from a lactic acid fermentation broth is provided. The method comprises the steps of contacting the lactic acid fermentation broth with functionalized silica comprising at least one hydrophobic ligand to facilitate binding of the 2,3-butanediol to the hydrophobic ligand, and separating the bound 2,3-butanediol from the lactic acid fermentation broth.

These and additional features and advantages will be more fully understood in view of the following detailed description.

Embodiments of the present invention are directed to a method of removing 2,3-butanediol from a lactic acid fermentation broth. The method comprises the steps of contacting the lactic acid fermentation broth with functionalized silica comprising at least one hydrophobic ligand to facilitate binding of the 2,3-butanediol to the hydrophobic ligand, and separating the bound 2,3-butanediol from the lactic acid fermentation broth. While we have emphasized the utilization of the functionalized silica to remove, vicinal diols, such as 2,3-butanediol, from the lactic acid fermentation broth, the removal of other impurities, contaminants, or microorganisms from the lactic acid fermentation broth are also contemplated herein. The separation is carried out using various methods, for example, by filtration, decantation, or centrifugation.

The functionalized silica may be provided using any filter media structure familiar to one of ordinary skill in the art. Particulates are captured on the filter media through a variety of mechanisms including physical entrapment, and binding to the media. The functionalized silica filter media capture contaminants, for example, by electrostatic, hydrophilic, hydrophobic, and/or covalent interactions, and/or by physical entrapment. By electrostatic interaction, the charged silica filter media bind to materials in a sample that have the opposite charge. By hydrophilic interaction, the portion of the silica filter media that has a strong affinity for water attracts the polar group of the materials by van der Waals interaction. By hydrophobic interaction, the portion of the silica filter media that contains long hydrocarbon chains attracts the nonpolar groups of the materials.

The structure of the filter media can be any form suitable for the application, such as granules, spheres, fibers, filaments, sheets, slabs, discs, blocks, films, and others. They can be manufactured into cartridges, disks, plates, membranes, woven materials, screens, etc. For example, bulk filtration may utilize plate and frame filter presses. Filter media can be loose particulate or structured material. The filter media are solid materials in a particulate form, insoluble in the liquid to be filtered; they are added to the liquid or are coated upon a filter or filter support. The purpose of using filter media is to speed up filtration, reduce fouling of the filter surface, reduce cracking of the filter layer, or otherwise to improve filtration characteristics. Filter media are often described according to their physical form. Some filter media are essentially discrete membranes, which function by retaining contaminants upon the surface of the membrane (surface filters). These filter media primarily operate via mechanical straining, and it is necessary that the pore size of the filter medium be smaller than the particle size of the contaminants that are to be removed from the fluid. Such a filter medium normally exhibits low flow rates and a tendency to clog rapidly.

Other filter media take the form of a porous cake or bed of fine fibrous or particulate material deposited on a porous support or substrate. The solution being filtered must wend its way through a path of pores formed in the interstices of the fine material, leaving particulate contaminants to be retained by the filter material. Because of the thickness of the filter material, the filters are called depth filters (as opposed to surface filters). The ability to achieve the required removal of suspended particulate contaminants with a filter medium of significantly larger pore size is attractive inasmuch as it allows higher flow rates. Furthermore, the filters have a higher capacity to retain particulates, thus having a reduced tendency to clog.

The functionalized silica filter media are treated by binding a functionalizing composition to the surface of the silica which is operable to bind with 2,3-butanediol. For binding purposes, the functionalizing composition comprises a hydrophobic ligand comprising at least one hydrocarbon chain. In exemplary embodiments, the silica may be functionalized by adding a predetermined amount of functional silane (or silanes) to the surface of the silica.

The silane-treated silica filter media have a similar or improved flow rate compared with non-treated silica filter media. Another advantage of the silane treated silica-based materials is the ability to modify the silica materials to increase their binding capacity without increasing filter aid load. In other words, the binding capacity of the silica filter media can be increased without significantly increasing the weight of silica materials.

The silica source may comprise numerous materials known to one skilled in the art. The silica may comprise amorphous silica, wherein the amorphous silica is typically of biogenic origin. Specifically, the amorphous silica may comprise rice hull ash, oat bran ash, wheat chaff ash, or combinations thereof. The silica may also comprises high pressure liquid chromatography (HPLC) grade silica, silica xerogels, silica hydrogels, fumed silica, silica fume, and other particulate silica materials known to one skilled in the art. The size of the particulates may vary; however, the particulates typically comprise particle sizes of up to about 500 μm, or up to about 250 μm, or about 10 μm to about 200 μm, or about 5 μm to about 75 μm, or about 25 to about 50 μm. The particulates may also comprise mixtures of any of the above described particulate materials.

Rice hull ash is a byproduct of rice farming. Each grain of rice is protected with an outer hull which accounts for 17-24% of the rough weight of the harvested product. Rice hulls consist of 71-87% (w/w) organic materials, such as cellulose and 13-29% (w/w) inorganic materials. A significant portion of the inorganic fraction, 87-97% (w/w) is silica ($SiO_2$). Currently, the inedible rice hulls are used as a source of fuel, fertilizer, and in insulation applications. When the rice hulls are burned, a structured silica material (often greater than 90%) can be produced as a byproduct. Rice hull ash (RHA) has larger surface area and more porous-channeled structure compared with other loose silica filter media. These characteristics make RHA one of the preferred treated filter substrates for use herein.

Diatomaceous earth (Diatomite) is a sedimentary silica deposit, composed of the fossilized skeletons of diatoms, one celled algae-like plants which accumulate in marine or fresh water environments. The honeycomb silica structures give diatomite useful characteristics such as absorptive capacity and surface area, chemical stability, and low bulk density. Diatomite contains 90% $SiO_2$ plus Al, Fe, Ca, and Mg oxides.

Perlite is a generic term for a naturally occurring siliceous volcanic rock that can be expanded with heat treatment. Expanded perlite can be manufactured to weigh as little as 2 pounds per cubic foot (32 kg/m3). Because perlite is a form of natural glass, it is classified as chemically inert and has a pH of approximately 7. Perlite consists of silica, aluminum, potassium oxide, sodium oxide, iron, calcium oxide, and magnesium oxide. After milling, perlite has a porous structure that is suitable for filtration of coarse microparticulates from liquids. It is suitable for depth filtration.

Talc (talcum) is a natural hydrous magnesium silicate, 3 $MgO.4SiO_2.H_2O$. Clay is hydrated aluminum silicate, $Al_2O_3.SiO_2.xH_2O$. Mixtures of the above silica filter media substrates can also be used to achieve the best filtration and cost performance. Any of the silica sources including rice hull ash and diatomaceous earth, may optionally undergo various purification and/or leaching steps before the surface silane treatment.

The specific surface area of the untreated silica filter media is preferred to be larger than 1 m2/g; more preferred to be larger than 10 m2/g. Silica filter media with a larger surface areas are preferable because they allow more silane ligands to be attached. In addition, media with large pores improve the filtration rate. However, larger pore materials have relatively lower surface area. The balance of large surface area and large pore size results in effective surface filtration treatment and filtration rate. The surface characteristics of these substrates can be evaluated by techniques such as NMR (Nuclear Magnetic Resonance), SEM (Scanning Electron Microscopy), BET (Brunauer-Emmett-Teller) surface area measurement technique, and carbon-hydrogen-nitrogen content can be determined by combustion techniques, which are well known to the art.

The silanes used to functionalize the silica materials may comprise any feasible organosilane, or mixtures of organosilanes. The silanes are of the structure $X_aR_bR_cR_dSi$, where X is a hydrolysable moiety chosen from halogens, preferably chloride, bromide or iodide and more preferably chloride, a hydrolyzable moiety chosen from alkoxy, alcohol, esters and amines bearing hydrogen atoms or bearing hydrocarbon radicals with homo atom or hetero atom chains ranging from about 1 to about 20, or from about 1 to about 8, or from about 1 to about 6, or from about 1 to about 4 including by not limited to methyl, methoxy, acetoxy, ethyl, ethoxy, propyl, propoxy, isopropyl, isopropoxy, butyl, iso-butyl, t-butyl, butoxy, iso-butoxy, t-butoxy and phenyl. The range for a can be from about 1 to about 3, and in some embodiments has a range of 3. R can be chosen from hydrocarbon radicals with homo atom or hetero atom chains ranging from about 1 to about 100, about 1 to about 30, about 1 to about 18, or about 1 to about 6 including alkyl, aryl, alkaryl, alkalkyl, alkylether, arylether, alkakylether, alkarylether, alkylester, arylester, alkalkylester, alkarylester, alkylamino, arylamino, alkarylamino, and more specifically include methyl, ethyl, propyl, iso-propyl, butyl, iso-butyl, t-butyl, pentyl and phenyl with the total of a+b+c+d equaling 4, preferably with b+c+d equaling 1.

Examples of silanes include Acetoxyethyldimethylchlorosilane, Acetoxyethylmethyldichlorosilane, Acetoxyethyltrichlorosilane, Acetoxymethyldimethylacetoxysilane, Acetoxymethyltriethoxysilane, Acetoxymethyltrimethoxysilane, Acetoxypropylmethyldichlorosilane, Acetoxypropyltrimethoxysilane, Benzyldimethylchlorosilane, Benzyltrichlorosilane, Benzyltriethoxysilane, Bis(methyldichlorosilyl)butane, Bis(methyldichlorosilyl)ethane, 1,2-Bis(trichlorosilyl)ethane. 1,8-Bis(trichlorosilyl)hexane. 1,9-Bis(trichlorosilyl)nonane, Bis(3-trimethoxysilyl)hexane, Bis[3-(trimethoxysilyl)propyl]ethylenediamine, 1,3-Bis(trimethylsiloxy)-1,3-dimethylsiloxane, n-Butyldimethylchlorosilane, n-Butyltrichlorosilane, t-Butyltrichlorosilane, 10-(Carbomethoxy)decyldimethylchlorosilane, 2-(Carbomethoxy)ethylmethyldichlorosilane, 2-(Carbomethoxy)ethyltrichlorosilane, 2-(Carbomethoxy)ethyltrichlorosilane, Carboxyethylsilanetriol Sodium Salt, 3-Chloropropylmethyldichlorosilane, 3-Chloropropylmethyldimethoxysilane, 3-Chloropropyltrichlorosilane, -Chloropropyltriethoxysilane, 3-Chloropropyltrimethoxysilane, 3-Cyanopropyldiisopropylchlorosilane, 3-Cyanopropyldimethylchorosilane, 3-Cyanopropyldimethylchlorosilane, 3-Cyanopropyltrichlorosilane, 3-Cyanopropyltriethoxysilane, 3-Cyanopropyltrimethoxysilane, n-Decyldimethylchorosilane, n-Decylmethyldichorosilane, n-Decyltrichorosilane, n-Decyltriethoxysilane, Di-n-Butyldichlorosilane, Diphenylmethylchlorosilane, Diphenylmethylethoxysilane, Diphenyldichlorosilane Diphenyldiethoxysilane, 1,7-Dichlorooctamethyltetrasiloxane, 1,5-Dichlorohexamethyltrisiloxane, 1,3-Dichlorotetramethyldisiloxane, (N,N-Dimethyl-3-aminopropyl)trimethoxysilane, Dimethyldichlorosilane, Dimethyldiethoxysilane, Dimethyldimethoxysilane, 3-(2,4-

Dinitrophenylamino)propyl-triethoxysilane, Di-n-Octyldichlorosilane, Diphenyldichlorosilane, Diphenyldiethoxysilane, Diphenyldimethoxysilane, 2-(3,4-Epoxycyclohexylethyl)trimethoxysilane, Ethyldimethylchlorosilane, Ethylmethyldichlorosilane, Ethyltrichlorosilane, Ethyltriethoxysilane, Ethyltrimethoxysilane, (3-Gylcidoxypropyl)triethoxysilane, (3-Gylcidoxypropyl)trimethoxysilane, (Heptadecafluoro-1,1,2,2-Tetrahydrodecyl)dimethylchlorosilane, (Heptadecafluoro-1,1,2,2-Tetrahydrodecyl)trichlorosilane, (Heptadecafluoro-1,1,2,2-Tetrahydrodecyl)triethoxysilane, (Heptadecafluoro-1,1,2,2-Tetrahydrodecyl)methyldichlorosilane, (3Heptafluoroisopropoxy)propyltrichlorosilane, n-Heptyldimethylchlorosilane, n-Heptylmethyldichlorosilane, n-Heptyltrichlorosilane, n-Hexadecyltrichlorosilane, n-Hexadecyltrimethoxysilane, Hexamethyldisilazane, Hexylmethyldichlorosilane, Hexyltrichlorosilane, Hexyltrimethoxysilane, 2-Hydroxy-4-(3-triethyoxysilylpropoxy)-diphenylketone, Isobutyldimethylchlorosilane, Isobutyltrichlorosilane, Isobutyltriethoxysilane, Isobutyltrimethoxysilane, 3-Isocyanatopropyltriethoxysilane, Isopropyldimethylchlorosilane, Isopropylmethyldichlorosilane, Mercaptomethylmethyldiethoxysilane, Mercaptopropylmethyldimethoxysilane, 3-Mercaptopropyltriethoxysilane, Mercaptopropyltriethoxysilane, Mercaptopropyltrimethoxysilane, 3-Mercaptopropyltrimethoxysilane, Methacryloxypropyltrichlorosilane, Methacryloxypropyltriethoxysilane, Methacryloxypropyltrimethoxysilane, 3-(p-Methoxyphenyl)propyltrichlorosilane, 3-Methoxypropyltrimethoxysilane, Methyltrichlorosilane, Methyltriethoxysilane, Methyltrimethoxysilane, n-Octadecyldiisobutyl(dimethylamino)silane, n-Octadecyldimethylchlorosilane, n-Octadecyldimethyl(dimethlamino)silane, n-Octadecyldimethylmethoxysilane, n-Octadecyldimethyl(3-trimethoxysilylpropyl)ammonium chloride, n-Octadecylmethyldichlorosilane, n-Octadecylmethyldiethoxysilane, n-Octadecyltrichlorosilane, n-Octadecyltriethoxysilane, n-Octadecyltrimethoxysilane, n-Octyldiisobutylchlorosilane, n-Octyldiisopropylchlorosilane, n-Octyldiisopropyl(dimethlamino)silane, n-Octyldimethylchlorosilane, n-Octyldimethylmethoxysilane, n-Octyldimethyldimethylaminosilane, n-Octylmethyldichlorosilane, n-Octylmethyldiethoxysilane, n-Octyltrichlorosilane, n-Octyltriethoxysilane, n-Octyltrimethoxysilane, n-Octyldiisopropylchlorosilane, Pentafluorophenyldimethylchlorosilane, Pentafluorophenylpropyldimethylchlorosilane, Pentafluorophenylpropyltrichlorosilane, Pentafluorophenylpropyltrimethoxysilane, Pentyltrichlorosilane, Pentyltriethoxysilane, Phenethyldiisopropylchlorosilane, Phenethyldimethylchlorosilane, Phenethylmethyldichlorosilane, Phenethyldimethyl(dimethylamino)silane, Phenethyltrichlorosilane, Phenethyltrimethoxysilane, 3-Phenoxypropyldimethylchlorosilane, 3-Phenoxypropyltrichlorosilane, Phenyldimethylchlorosilane, Phenylmethyldichlorosilane, Phenylmethyldiethoxysilane, Phenylmethylmethoxysilane, Phenylpropyldimethylchlorosilane, Phenylpropylmethyldichlorosilane, Phenyltrichlorosilane, Phenyltriethoxysilane, Phenyltrimethoxysilane, n-Propyldimethylchlorosilane, n-Propylmethyldichlorosilane, n-Propyltrichlorosilane, n-Propyltriethoxysilane, n-Propyltrimethoxysilane, Tetrachlorosilane, Tetraethoxysilane, 2,2,5,5-Tetramethyl-2,5-disila-1-aza-cyclopentane, Triacontyldimethylchlorosilane, Triacontyltrichlorosilane, (Tridecafluororo-1,1,2,2-tetrahydrooctyl)dimethylchlorosilane, (Tridecafluororo-1,1,2,2-tetrahydrooctyl)methyldichlorosilane, (Tridecafluororo-1,1,2,2-tetrahydrooctyl)trichlorosilane, (Tridecafluororo-1,1,2,2-tetrahydrooctyl)triethoxysilane, Triethyoxysilylpropylethylcarbamate, N-(3-riethoxysilylpropyl)gluconamide, N-(3-Triethyoxysilylpropyl)-4-hydroxy-butyramide, N-(Triethoxysilylpropyl)-O-polyethylene oxide, 3-(Triethyoxysilylpropyl)succinic anhydride, Triethylacetoxysilane, Triethylchlorosilane, (3,3,3-Trifluoropropyl)dimethylchlorosilane, (3,3,3-Trifluoropropyl)methyldichlorosilane, (3,3,3-Trifluoropropyl)trichlorosilane, (3,3,3-Trifluoropropyl)trimethoxysilane, 2-(Trimethoxysilylethyl)pyridine, Trimethylchlorosilane, Trimethylethoxysilane, Trimethylmethoxysilane, Tri-n-propylchlorosilane, Undecyltrichlorosilane, Ureidopropyltriethoxysilane, Ureidopropyltrimethoxysilane, Vinylmethyldichlorosilane, Vinylmethyldiethoxysilane, Vinylmethyldimethoxysilane, Vinyltrichlorosilane, Vinyltriethoxysilane, Vinyltrimethoxysilane.

Silanes most useful for treating silica in this invention preferably have one or more moieties selected from the group consisting of alkoxy, quaternary ammonium, aryl, epoxy, amino, urea, methacrylate, imidazole, carboxy, carbonyl, isocyano, isothiorium, ether, phosphonate, sulfonate, urethane, ureido, sulfhydryl, carboxylate, amide, carbonyl, pyrrole, and ionic.

Examples for silanes having an alkoxy moiety are mono-, di-, or trialkoxysilanes, such as n-octadecyltriethoxysilane, n-octytriethoxysilane and phenyltriethoxysilane. Examples of silanes having a quaternary ammonium moiety are 3-(trimethoxysilyl)propyloctadecyldimethylammoniumchloride, N-trimethoxysilylpropyl-N,N,N-trimethylammoniumchloride, or 3-(N-styrylmethyl-2-aminoethylamino)-propyltrimethoxysilane hydrochloride. Examples of silanes having an aryl moiety are 3-(trimethoxysilyl)-2-(p,m-chlandomethyl)-phenylethane, 2-hydroxy-4-(3-triethoxysilylpropoxy)-diphenylketone, ((chloromethyl)phenylethyl)trimethoxysilane and phenyldimethylethoxysilane. Examples of silanes having an epoxy moiety are 3-glycidoxypropyltrimethoxysilane and 2-(3,4-epoxycyclohexyl)ethyltrimethoxysilane. Examples of silanes having an amino moiety are 3-aminopropyltrimethoxysilane, N-(2-aminoethyl)-3-aminopropyltrimethoxysilane, trimethoxysilylpropyldiethylenetriamine, 2-(trimethoxysilylethyl)pyridine, N-(3-trimethoxysilylpropyl)pyrrole, trimethoxysilylpropyl polyethyleneimine, bis-(2-hydroxyethyl)-3-aminopropyltriethoxysilane, and bis(2-hydroxyethyl)-3-aminopropyltriethoxysilane.

Examples of silanes having a urea moiety are N-(triethoxysilylpropyl)urea and N-1-phenylethyl-N'-triethoxysilylpropylurea. An example of silanes having a methacrylate moiety is 3-(trimethoxysilyl)propyl methacrylate. An example of silanes having a sulfhydryl moiety is 3-mercaptopropyltriethoxysilane. Examples of silanes having an imidazole moiety are N-[3-(triethoxysilyl)propyl]imidazole and N-(3-triethoxysilylpropyl)-4,5-dihydroimidazole. Examples of ionic silanes are 3-(trimethoxysilyl)propyl-ethylenediamine triacetic acid trisodium salt; and 3-(trihydroxysilyl)propylmethylphosphonate sodium salt. An examples of silanes having a carbonyl moiety is 3-(triethoxysilyl)propylsuccinic anhydride. Examples of silanes having an isocyano moiety are tris(3-trimethoxysilylpropyl)isocyanurate and 3-isocyanatopropyltriethoxysilane. Examples of silanes having an ether moiety are bis[(3-methyldimethoxysilyl)propyl]-polypropylene oxide and N-(triethoxysilylpropyl)-O-polyethylene oxide urethane. An example of a silane having a sulfonate moiety is 2-(4-chlorosulfonylphenyl)-ethyltrichlorosilane. An example of a silane having a isothiourium moiety is trimethoxysilylpropylisothiouronium chloride. Examples of silanes having an amide moiety are triethoxysilylpropylethylcarbamate, N-(3-triethoxysilylpropyl)-gluconamide, and N-(triethoxysilylpropyl)-4-hydroxybutyramide. Examples of silanes having a urethane moiety are N-(triethoxysilylpropyl)-O-polyethylene oxide urethane and O-(propargyloxy)-N-(triethoxysilylpropyl)urethane.

Silica filter media can also be treated with more than one silane such as N-trimethoxysilylpropyl-N,N,N-trimethylammonium chloride and bis(2-hydroxyethyl)-3-aminopropyltriethoxysilane; 3-aminopropyltrimethoxysilane and N-(triethoxysilylpropyl)-O-polyethylene oxide urethane; 3-trihydrosilylpropylmethylphosphonate, sodium salt and N-(triethoxysilylpropyl)-O-polyethylene oxide urethane; N-trimethoxysilylpropyl-N,N,N-Cl, trimethylammonium chloride and (3-glycidoxypropyl)trimethoxysilane; 3-trihydrosilylpropylmethylphosphonate, sodium salt and bis-(2-hydroxyethyl)-3-aminopropyltriethoxysilane; 3-(N-styrylmethyl-2-aminoethylamino)-propyltrimethoxysilane hydrochloride and N-(triethoxysilylpropyl)-O-polyethylene oxide urethane; 2-(trimethoxysilylethyl)pyridine and N-(3-triethoxysilylpropyl)-gluconamide; N-trimethoxysilylpropyl-N,N,N-Cl, trimethylammonium chloride and N-(3-triethoxysilylpropyl)-gluconamide; N-trimethoxysilylpropyl-N,N,N-Cl, trimethylammonium chloride and 2-hydroxy-4-(3-triethoxysilylpropoxy)-diphenylketone; 3-mercaptopropyltriethoxysilane and N-(triethoxysilylpropyl)-O-polyethylene oxide urethane; 3-(triethoxysilyl)propylsuccinic anhydride and N-(triethoxysilylpropyl)-O-polyethylene oxide urethane; trimethoxysilylpropyl-ethylenediamine, triacetic acid, trisodium salt and N-(triethoxysilylpropyl)-O-polyethylene oxide urethane; 2-(4-chlorosulfonylphenyl)-ethyltrichlorosilane and N-(triethoxysilylpropyl)-O-polyethylene oxide urethane; and 2-(4-chlorosulfonylphenyl)-ethyltrichlorosilane and bis-(2-hydroxyethyl)-3-aminopropyltriethoxysilane.

In a further embodiment of the method, the silane containing material may optionally include a solvent, such as ethanol. Solvents suitable for this include ethanol, methanol, butanol, pentanol, hexanol, heptanol, octanol, nonanol, decanol and other higher boiling alkyl alcohols, toluene, xylene, and other aromatic solvents, glyme, diglyme, ethyl ether, pentane, hexane, heptane, octane, nonane, decane and other higher boiling hydrocarbon solvents, tetrahydrofuran, furan, or other solvents known to one skilled in the art.

The functionalizing of silica is an established process. Most silicas are treated in a "wet" process. The "wet" process is a silane functionalization process, which utilizes a solvent to effectively slurry an entire load of particulates. The majority of the weight of a processed mass, which includes particulates, additives, and solvent, is composed of solvent. A high solvent concentration is designed to promote the intimate contact of the reactive additive i.e., silane and the surface of the particulates with the goal of initiating a reaction between the additive and some reactive site on the surface. Generally, the wet process requires a relatively long batch time, typically ranging from 1-24 hours at higher than ambient temperature, to complete the reaction. Multiple additional washing steps may be utilized.

Alternatively, a "dry" process may be used to functionalize silica. In the dry process, the silane additive is provided to a mixture that is mostly composed of materials with which it will react, as opposed to the "wet" process where most of the processed mass is a solvent that is inert to reaction with the specific additive. The dry process utilizes a mixing device capable of stirring the silica and silane to promote attach without significant amounts of solvent.

While not being bound by theory, the functionalized silica filter media of the present invention is designed to prefer vicinal diols, such as 2,3-butanediol (BDO), over the lactic acid or its salt in the fermentation broth. Lactic acid and BDO have a hydrophilic nature; however, the lactic acid, which is in the salt form, is more highly ionic and includes greater water solubility than the diol. As a result, the diol differentiates itself from the lactic acid by seeking a less aqueous environment. Consequently, utilizing a functionalized silica with a hydrophobic ligand causes the diol to migrate from the aqueous phase to the functionalized silica filter media.

In one or more embodiments, a C4 to a C18 hydrocarbon chain may be utilized for the hydrophobic ligand. In a specific embodiment, the hydrophobic ligand is a C8 hydrocarbon chain. C8 hydrocarbon chains are advantageous for separations of organic molecules in highly aqueous matrices, because C8 hydrocarbons are hydrophobic while being less susceptible to chain collapse. A C8 chain does not collapse as readily as other longer simple hydrocarbon chains, and is more soluble than other longer hydrocarbon chains in aqueous chromatographic matrices.

One alternative to C4-C18 hydrocarbon chains which avoid chain collapse are polar embedded organofunctional structures. Polar embedded structures are those that contain both an acidic hydrogen moiety, such as amino or hydroxyl, and the hydrophobic moiety on a single organofunctional chain. The acid portion is usually located on the middle portion of the chain followed by the terminal hydrophobic portion. Examples of these polar embedded structures are provided in U.S. Pat. No. 7,125,488. This configuration keeps the chain from folding on itself, leaving the chains less accessible for molecule capture by dissolving into the chains. Another alternative operable for avoiding chain collapse is the use of mixed phase compositions. Mixed phase compositions are composed of two or more different silanes, preferably one hydrophobic and one hydrophilic. Examples of these mixed phase compositions are provided in U.S. Pat. No. 5,922,449. These compositions tend to suffer less chain collapsing due to disruption of chain stacking.

EXAMPLES

The following experiment, which is described in detail below, demonstrates the removal of BDO achieved with 8 different filter media compositions. As will be shown below, the C8 hydrocarbon chain provided the best removal of BDO among the tested compositions.

The following stepwise procedure was used to prepare a simulated lactic acid broth. 1000 mL of deionized water was loaded into a ½-gallon glass jug with magnetic stirrer. 75 g of Calcium L-lactate hydrate, as purchased from Aldrich Chemicals, was added to the water, and was stirred until the Calcium L-lactate was dissolved. Using an eyedropper, 0.88 grams of 2,3-Butanediol, were added and stirred an additional 15 minutes to assure all ingredients were well blended. This yielded a solution of about 818 ppm BDO.

For the treatment of the simulated lactic acid broth, 1 gram of media was mixed with 10 mL of the lactic acid solution in a 20 dram vial and shaken for 30 minutes on a laboratory wrist shaker. The mixture was then filtered into a 10 dram vial using a 0.45 micron syringeless disposable filter device (Whatman product #AV1254PP and lot #M722 purchased from Fisher Scientific). Then, the samples were filtered and analyzed using a gas chromatograph.

The samples were analyzed by treating 0.1 g of sample with a known amount of n-butanol (ca. 300 micrograms) as an internal standard. The samples were then treated with 2 grams of MeOH and the samples were analyzed without further dilution on a gas chromatograph equipped with a flame ionization detector. Standard solutions of n-butanol in methanol were prepared and were analyzed in the same manner as the unknowns. The experimental response factor of 2,3-butanediol (the two butanediol peaks were treated as a group) relative to butanol was determined from a two-point calibration. This same experimental response factor was used to determine the level of 2,3-butanediol in the unknowns. The experimental results are provided in Table 1 below.

TABLE 1

| Run No. | Silica Type | Silica SA ($m^2$g) | Silane Treatment Product Number | Silane Names | Silane Treatment (mol %) | % Carbon | ppm BDO by GC* | Normalized % Remaining |
|---|---|---|---|---|---|---|---|---|
| 1 | No silica | | | | | | 690 | 100 |
| 2 | Precipitated | 535 | Z-6032 & SIB1140 | 3-(N-styrylmethyl-2-aminoethylamino)-propyltrimethoxysilane hydrochloride & Bis-(2-hydroxyethyl)-3-aminopropyltriethoxysilane | 50/50 | 8.33 | 593 | 86 |
| 3 | Xerogel | 698 | SIT8378.3 | 3-(Trihydroxysilyl)-1-Propanesulfonic Acid | 100 | 2.28 | 594 | 86 |
| 4 | Hydrogel | 800 | Z-6020 & SIP6731.6 | Aminoethylaminopropyltrimethoxysilane & (S)-N-1-Phenylethyl-n'-triethoxysilylpropylurea | 50/50 | 19.87 | 601 | 87 |
| 5 | Xerogel | 698 | SIB1140.0 & SIT8402.0 | Bis-(2-hydroxyethyl)-3-aminopropyltriethoxysilane & N-(Trimethoxysilylpropyl)ethylenediamine Triacetic Acid, Sodium Salt | 50/50 | 8.27 | 726 | 105 |
| 6 | Rice Hull Ash | 300 | Z-6032 & Z-6020 | 3-(N-styrylmethyl-2-aminoethylamino)-propyltrimethoxysilane hydrochloride & Aminoethylaminopropyltrimethoxysilane | 75/25 | 8.12 | 510 | 74 |
| 7 | Xerogel | 325 | Z-6032 & Z-6020 | 3-(N-styrylmethyl-2-aminoethylamino)-propyltrimethoxysilane hydrochloride & Aminoethylaminopropyltrimethoxysilane | 25/75 | No data | 541 | 78 |
| 8 | Hydrogel | 800 | Z-6341 | n-Octyltriethoxysilane | 100 | 9.37 | 450 | 65 |
| 9 | Hydrogel | 800 | Z-6032, Z-6020 & Z-6341 | 3-(N-styrylmethyl-2-aminoethylamino)-propyltrimethoxysilane hydrochloride & Aminoethylaminopropyltrimethoxysilane & n-Octyltriethoxysilane | 33/33/33 | 9.87 | 626 | 91 |

As shown, Run Nos. 6, 7, and 8, whose structures are shown below, reduced the amount of BDO remaining in the synthetic broth down to about 74%, 78%, and 65%, respectively. These media were hydrophobic in nature, with the best results coming from the octyl (C8) functional media, Run 7 at 65%.

3-[N-styrylmethyl-2-aminoethylamino]-propyltrimethoxysilane hydrochloride

Aminoethylaminopropyltrimethoxysilane n-Octyltriethoxysilane

It is noted that terms like "specifically," "preferably," "commonly," and "typically" and the like, are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A method of removing vicinal diols from a lactic acid fermentation broth comprising:
    contacting the lactic acid fermentation broth with functionalized silica comprising at least one hydrophobic ligand to facilitate binding of vicinal diols to the hydrophobic ligand; and
    separating the contacted lactic acid fermentation broth from the functionalized silica to remove vicinal diols.

2. The method of claim 1 wherein the vicinal diols comprise 2,3 diols.

3. The method of claim 1 wherein the vicinal diols comprise 2,3 butanediol.

4. The method of claim 1 wherein the separating occurs via filtration, decantation, screening, centrifuging, or combinations thereof.

5. The method of claim 1 wherein the hydrophobic ligand comprises at least one hydrocarbon chain.

6. The method of claim 5 wherein the hydrocarbon chain is a C4 to a C18 hydrocarbon chain.

7. The method of claim 1 wherein the hydrophobic ligand is a $C_8$ hydrocarbon chain.

8. The method of claim 1 wherein the functionalized silica is an amorphous silica.

9. The method of claim 8 wherein the amorphous silica of biogenic origin.

10. The method of claim 8 wherein the amorphous silica comprises rice hull ash, oat bran ash, wheat chaff ash, or combinations thereof.

11. The method of claim 1 wherein the functionalized silica comprises high-pressure liquid chromatography (HPLC) grade silica.

12. The method of claim 1 further comprising utilizing the functionalized silica to remove microorganisms from the lactic acid fermentation broth.

13. The method of claim 1 wherein the functionalized silica comprises silane which reacts with the functionalized silica on the silica surface.

14. The method of claim 13 wherein the silane comprises hydrolyzable moiety selected from the group consisting of alkoxy, halogen, hydroxy, aryloxy, amino, amide, methacrylate, mercapto, carbonyl, urethane, pyrrole, carboxy, cyano, aminoacyl, acylamino, alkyl ester, and aryl ester.

15. The method of claim 13 wherein the silane comprises alkoxysilane.

16. The method of claim 13 wherein the silane has an additional moiety selected from the group consisting of quaternary ammonium, aryl, epoxy, amino, urea, methacrylate, imidazole, carbonyl, isothiorium, sulfonate, phosphonate, urethane, ureido, isocyano, sulfhydryl, carboxylate, carbonyl, amide, carbonyl, urethane, pyrrole, and ionic moiety.

17. The method of claim 1 wherein at least 40% of the vicinal diols is removed from the lactic acid fermentation broth.

18. The method of claim 1 wherein at least 20% of the vicinal diols is removed from the lactic acid fermentation broth.

* * * * *

UNITED STATES PATENT AND TRADEMARK OFFICE
CERTIFICATE OF CORRECTION

PATENT NO.      : 8,293,939 B2
APPLICATION NO. : 13/255421
DATED           : October 23, 2012
INVENTOR(S)     : Evans et al.

It is certified that error appears in the above-identified patent and that said Letters Patent is hereby corrected as shown below:

In column 11, line 4 (claim 7, line 2), please delete the "$C_8$" and insert -- C8 --, therefor.

Signed and Sealed this
Twenty-sixth Day of February, 2013

Teresa Stanek Rea
*Acting Director of the United States Patent and Trademark Office*